(12) United States Patent
Desfougeres et al.

(10) Patent No.: US 9,790,511 B2
(45) Date of Patent: Oct. 17, 2017

(54) YEAST STRAINS FOR THE PRODUCTION OF BIOMASS ON A SUBSTRATE COMPRISING A C5 SUGAR

(71) Applicant: LESAFFRE ET COMPAGNIE, Paris (FR)

(72) Inventors: Thomas Desfougeres, Neuville en Ferrain (FR); Georges Pignede, Marcq-en-Baroeul (FR)

(73) Assignee: LESAFFRE ET COMPAGNIE, Paris (FR)

( * ) Notice: Subject to any disclaimer, the term of this patent is extended or adjusted under 35 U.S.C. 154(b) by 206 days.

(21) Appl. No.: 14/435,217

(22) PCT Filed: Oct. 8, 2013

(86) PCT No.: PCT/FR2013/052391
§ 371 (c)(1),
(2) Date: Apr. 13, 2015

(87) PCT Pub. No.: WO2014/060678
PCT Pub. Date: Apr. 24, 2014

(65) Prior Publication Data
US 2015/0259694 A1   Sep. 17, 2015

(30) Foreign Application Priority Data
Oct. 16, 2012   (FR) ..................... 12 59836

(51) Int. Cl.
| | |
|---|---|
| *C12N 1/16* | (2006.01) |
| *C12N 15/81* | (2006.01) |
| *C12R 1/865* | (2006.01) |
| *C12N 1/22* | (2006.01) |
| *C12N 15/01* | (2006.01) |
| *C12P 7/10* | (2006.01) |
| *C12N 9/04* | (2006.01) |
| *C12N 9/12* | (2006.01) |
| *C12N 9/92* | (2006.01) |
| *A21D 8/04* | (2006.01) |
| *C12N 1/18* | (2006.01) |
| *C12N 9/90* | (2006.01) |

(52) U.S. Cl.
CPC ............ *C12N 15/81* (2013.01); *A21D 8/047* (2013.01); *C12N 1/18* (2013.01); *C12N 1/22* (2013.01); *C12N 9/0006* (2013.01); *C12N 9/1205* (2013.01); *C12N 9/90* (2013.01); *C12N 9/92* (2013.01); *C12N 15/01* (2013.01); *C12P 7/10* (2013.01); *C12R 1/865* (2013.01); *C12Y 101/01021* (2013.01); *C12Y 101/01175* (2013.01); *C12Y 101/01307* (2013.01); *C12Y 207/01017* (2013.01); *C12Y 503/01005* (2013.01); *Y02E 50/16* (2013.01); *Y02E 50/17* (2013.01)

(58) Field of Classification Search
CPC ....................................................... C12N 1/16
USPC ...................................................... 435/252.3
See application file for complete search history.

(56) References Cited

U.S. PATENT DOCUMENTS

| 2012/0142067 A1 | 6/2012 | Desfougeres et al. |
| 2013/0040353 A1 | 2/2013 | Desfougeres et al. |

FOREIGN PATENT DOCUMENTS

| WO | 2011/003893 A1 | 1/2011 |
| WO | 2011/128552 A1 | 10/2011 |
| WO | 2011/131667 A1 | 10/2011 |
| WO | 2012/072793 A1 | 6/2012 |

OTHER PUBLICATIONS

French Search Report issued in corresponding application No. 1259836 (dated 2013).
International Search Report issued in application No. PCT/FR2013/052391 dated Feb. 3, 2014.
Attfield, Paul V., et al., "Use of population genetics to derive nonrecombinant *Saccharomyces cerevisiae* strains that grow using xylose as a sole carbon source", FEMS Yeast 6 (2005) p. 862-868.
Hahn-Hägerdal, Bärbel, et al., Metabolic Engineering of *Saccharomyces cerevisiae* of Xylose Utilization, Advances in Biochemical Engineering/Biotechnology, vol., 73, 2001, p. 53-84.
Karhumaa, Kaisa, et al., "Investigation of limiting metabolic steps in the utilization of xylose by recombinant *Saccharomyces cerevisiae* using metabolic engineering", Yeast, 2005: 22: p. 359-368.

*Primary Examiner* — Maryam Monshipouri
(74) *Attorney, Agent, or Firm* — Sughrue Mion, PLLC

(57) ABSTRACT

The present invention concerns novel *Saccharomyces cerevisiae* yeast strains capable of multiplying on a substrate comprising at least one C5 sugar with a speed and rate of multiplication compatible with the industrial production of yeast. It also concerns novel strains which, when cultured, make it possible to obtain yeasts having an application efficiency, i.e. an efficiency that is satisfactory in applications and uses of interest in industries such as breadmaking, biomass production, flavour production, the production of secondary metabolites, protein production, ethanol production, brewing, winemaking or the production of yeast extract.

11 Claims, 4 Drawing Sheets

SEQUENCE LISTING

```
<160> NUMBER OF SEQ ID NOS: 3

<210> SEQ ID NO 1
<211> LENGTH: 23
<212> TYPE: DNA
<213> ORGANISM: Saccharomyces cerevisiae

<400> SEQUENCE: 1
agtcacatca agatcgttta tgg                                       23

<210> SEQ ID NO 2
<211> LENGTH: 23
<212> TYPE: DNA
<213> ORGANISM: Saccharomyces cerevisiae

<400> SEQUENCE: 2
gcacggaata tgggactact tcg                                       23

<210> SEQ ID NO 3
<211> LENGTH: 23
<212> TYPE: DNA
<213> ORGANISM: Saccharomyces cerevisiae

<400> SEQUENCE: 3
actccacttc aagtaagagt ttg                                       23
```

YEAST STRAINS FOR THE PRODUCTION OF BIOMASS ON A SUBSTRATE COMPRISING A C5 SUGAR

CROSS REFERENCE TO RELATED APPLICATIONS

This is a National Stage of International Application No. PCT/FR2013/052391 filed Oct. 8, 2013, claiming priority based on French Patent Application No. 12 59836 filed Oct. 16, 2012, the contents of all of which are incorporated herein by reference in their entirety.

TECHNICAL FIELD

The present invention relates to the field of biomass production, in particular yeast production. It concerns particularly the production of yeasts on a substrate comprising at least one C5 sugar and more particularly the production of yeasts on a substrate originating from the hydrolysis of lignocellulosic materials. It also concerns the use of yeasts produced in applications for the yeast industry, such as breadmaking, biomass production, flavor production, the production of secondary metabolites, protein production, RNA production, ethanol production, brewing or the production of yeast extract.

Technological Background and Problem to be Solved

For their multiplication by a process of aerobic respiration, the yeasts need:
- carbon compounds as carbon and energy source,
- reduced nitrogen compound in the form of ammonium; however, some yeasts are capable of using oxidized compounds (such as nitrates) or organic compounds for the synthesis of proteins and nucleic acids,
- various mineral elements, and vitamins and growth factors which vary depending on the yeasts.

If the yeast is produced on a medium with a defined composition, based, for example, on glucose or fructose syrups as carbon substrate, and ammonium and phosphorus salts as nitrogen and phosphate sources, the culture medium will have to be supplemented by an addition of mineral salts, of vitamins and of trace elements, which makes the production complex and expensive.

Beet and cane sugar refinery molasses consist of sugars (glucose and fructose), of organic compounds and of mineral compounds. This is the reason why these molasses are the substrates of choice from the economical and technical standpoint and why, to date, they are the main raw material used for the industrial production of yeasts.

However, the decreased availability of cane or beet molasses, connected in particular with their massive use for the production of bioethanol, endangers this type of production. Consequently, it is necessary to find new carbon substrates as a substitute for the sucrose provided from molasses.

Now, the industrial production of bioethanol, in particular second-generation bioethanol, has revealed the availability of other sources of fermentation substrates. Indeed, the industry of second-generation bioethanol uses lignocellulosic materials derived from plants. These materials, which represent the vast majority of plants, consist of cellulose, hemicellulose and lignin. After hydrolysis, the lignocellulosic materials lead to a mixture of C6 sugars (6 carbon atoms) and C5 sugars (5 carbon atoms).

All the yeasts are capable of metabolizing C6 sugars; C5 sugars, on the other hand, are generally poorly suited for fermentation or cannot be fermented by yeasts of the genus Saccharomyces, in particular Saccharomyces cerevisiae (Sc).

The recent literature pertaining to the production of second-generation bioethanol describes Sc yeasts that have been modified to make them capable of fermenting C5 sugars. Among these documents, one can cite, for example, WO 2011/128552 and WO 2012/72793 in the name of the applicant.

WO 2011/128552 describes a yeast strain obtained by a method for genetic modification, comprising introducing into the genome of the strain a gene coding for a Xylose reductase (XR) and a gene coding for a Xylose dehydrogenase (XDH).

WO 2012/72793 describes a yeast strain obtained by a method including introducing into the genome of the strain a copy of an exogenous gene coding for a xylose isomerase, said gene originating preferably from *Clostridium phytofermentans*, and at least one copy of a gene coding for xylitol dehydrogenase, said gene originating from *Pichia stipitis*.

Although the strains described in these documents are capable of multiplying on a substrate comprising C5 sugar, the inventors of the present invention have observed that the speed of multiplication on a substrate consisting of or comprising a C5 sugar remains low and in any case is incompatible with an industrial production of yeasts.

In addition, the inventors observed that, during their final industrial use, for example, as yeasts in fermentation for breadmaking or yeasts intended for the production of yeast extracts, etc., the yeasts thus obtained presented a reduced efficiency in comparison to the efficiency of the yeasts obtained from the unmodified original strains.

Thus, there is a real demand for novel strains for the production of yeasts that make it possible to completely or partially replace the C6 sugars as carbon substrate, with yeast production yields compatible with economic and industrial exploitation. In addition, culturing such yeasts should lead to yeasts having an efficiency in their final industrial use that is of great interest and entirely satisfactory.

SUMMARY OF THE INVENTION

The subject matter of the present invention relates to novel Sc yeast strains capable of multiplying on a substrate comprising at least one C5 sugar at a speed and rate of multiplication compatible with the industrial production of yeast.

It also relates to novel strains which, when cultured, make it possible to obtain yeasts having an application efficiency, i.e. an efficiency that is satisfactory in their final industrial use, i.e. at least equal to 80%, preferably 95% and even more preferably 105% of the reference application efficiency.

Another subject matter of the invention is a method for obtaining a yeast strain according to the invention by genetic modification or by hybridization.

Another subject matter of the invention is the use of yeasts obtained by the method of the invention and/or of novel yeasts in an industrial application selected from breadmaking, biomass production, flavor production, the production of secondary metabolites, protein production, RNA production, ethanol production, brewing, winemaking or the production of yeast extract.

DETAILED DESCRIPTION OF THE INVENTION

Figure 1:
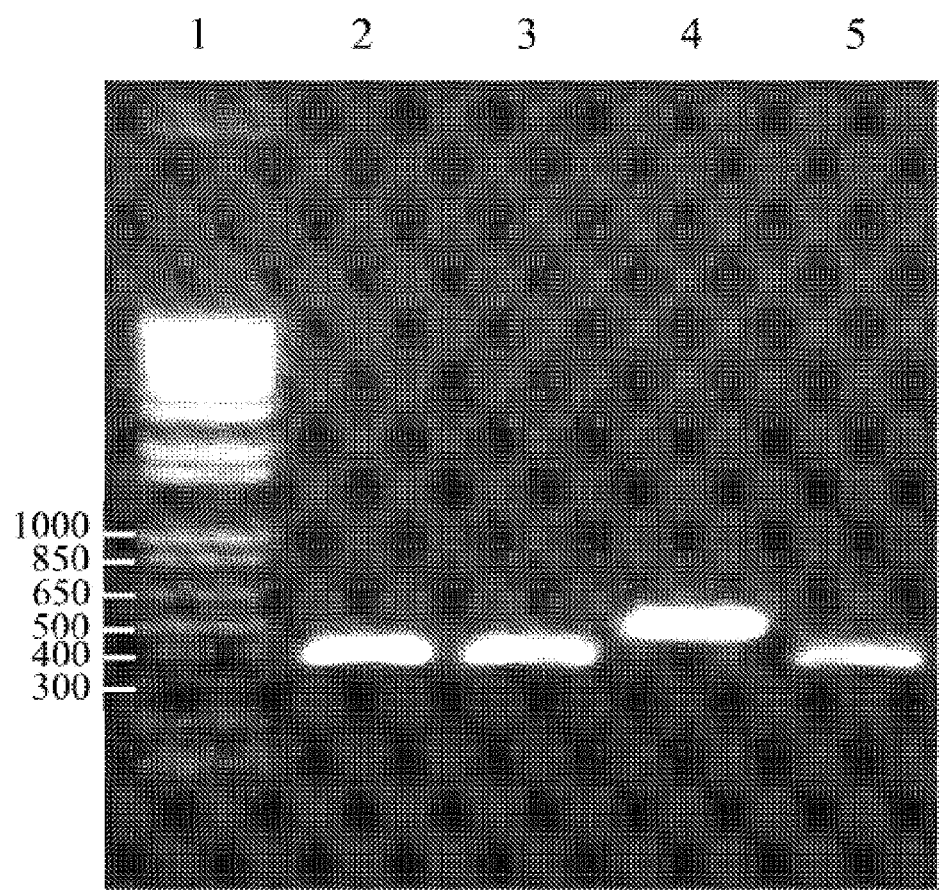
FIG. 1 is the result of a PCR analysis of Example 1. The values indicated on the left portion of the gel correspond to the size of the DNA fragments of the size marker, and are expressed in base pairs (lane 1). Lanes 2 to 5 correspond to X1051, X1052, Mat a Control and Mat alpha Control, respectively.

The present invention relates to a yeast strain capable of multiplying under aerobic conditions on a substrate comprising at least one C5 sugar, characterized in that it satisfies a growth test on xylose or in that it has a maximum speed of multiplication such that it satisfies a growth test on CP medium.

Growth Test on Xylose:

This test consists of monitoring over time by spectrophotometry at a wavelength of 600 nm the variation in turbidity of a solution containing 50 mL of YFX culture medium inoculated with $10^8$ strain cells to be tested at 30° C. under constant stifling at 150 rpm. The test is satisfied when the Optical Density (OD) at 24 h is greater than 2, and is at least 3, preferably at least 10 at 48 h.

The YFX medium is as defined below:

| YFX | g/kg | mL |
|---|---|---|
| Distilled water qs | 1000 | |
| Xylose | 70 | |
| EXL type J | 5 | |
| DAP | 4.7 | |
| Citric acid | 11.4 | |
| Trisodium citrate | 13.5 | |
| ZnSO4 (10.6 g/L) | | 2 |
| MgSO4 7H2O (400 g/L) | | 2.5 |
| Thiamine Vit B1 (18.24 g/L) | | 1 |
| Pyridoxine Vit B6 (5.28 g/L) | | 1 |
| Biotin (1.76 g/L) + KOH | | 1 |
| Pantothenate (3.8 g/L) | | 1 |
| Nicotinic acid (4 g/L) | | 4 |
| Meso-inositol (50 g/L) | | 1 |
| Riboflavin (1 g/L) | | 1 |
| Paraaminobenzoate (1.2 g/L) | | 1 |
| Tween 80 | | 1 |

Growth Test on CP Medium:

This test consists of monitoring over time by spectrophotometry at a wavelength of 600 nm the variation in turbidity of a solution containing 50 mL of CP culture medium which contains 10 g/kg of EXL type J100 (Biospringer) and 10 g/kg of bactopeptone as well as 100 g/kg of sucrose, said medium being inoculated with $10^8$ cells to be tested at 30° C. under constant stirring at 150 rpm. The test is satisfied if the variation in OD is exponential between 3.5 and 7.5 hours. The equation which then represents the variation in OD has the form $OD_{tf} = OD_{ti}\ e^{n(tf-ti)}$ where n is between 0.35 and 0.9, preferably between 0.45 and 0.80, and preferentially between 0.65 and 0.75.

According to an advantageous embodiment, the strains according to the invention satisfy both the growth test on xylose and the growth test on CP medium.

According to the invention, the yeast strain is selected from the genus *Saccharomyces* and it is preferably *Saccharomyces cerevisiae*.

According to the invention, C5 sugar refers to a monosaccharide comprising 5 carbon atoms or pentose. The C5 sugar is selected from the group comprising arabinose, xylose and their mixtures. Preferably, the C5 sugar is xylose.

According to the invention, the substrate comprising at least one C5 sugar also comprises at least one C6 sugar, i.e. a monosaccharide comprising 6 carbon atoms or hexose. The C6 sugar is selected from the group comprising glucose, fructose, galactose, mannose or originating from the degradation of disaccharide such as sucrose, maltose, trehalose, isomaltose or their mixtures.

Preferably, the substrate of the invention includes at least one C5 sugar and at least one C6 sugar in a C5/C6 ratio between 0.1 and 2.

The yeasts obtained by the multiplication of the strains according to the invention have useful performances for industrial applications such as breadmaking, biomass production, flavor production, the production of secondary metabolites, protein production, ethanol production, brewing, winemaking or the production of yeast extract. In other words, the yeasts obtained by culturing the strains according to the invention are efficient in the final industrial use for which they are intended. This efficiency is referred to as "application efficiency" in the present patent application.

For all the industrial uses considered, it is necessary that the yeasts obtained by culturing the strains of the invention are not damaged during drying, i.e. that less than 20% of the yeasts are inactivated after a drying.

According to a particular embodiment, the strains according to the invention are such that they satisfy the following drying test:

The biomass obtained after culturing is separated from the medium by centrifugal separation optionally using washing steps in order to obtain a concentrated yeast suspension at 18-22% of dry extract ("yeast cream").

This suspension is subjected to a step of dehydration by filtration in order to obtain a pasty mass ("pressed yeast") at 28-34% of dry extract.

This composition then is subjected to a process for forming sausage-like pieces (extrusion) to obtain thin sausage-like pieces (vermicelli-like pieces) having a diameter of 0.2 to 2 mm, which are dried by a hot air current in a dryer with fluidized air bed.

The drying conditions (temperature schedule) are controlled rigorously so that the temperature of the product is always less than 50° C. The final dry yeast, which is in the form of fine vermicelli-like pieces, has a dry extract content of at least 95%.

In order to improve the viability of the cells of dry yeast, one can add to the yeast (suspension or pressed yeast) additives with a protective effect, such as emulsifiers, at 0.2 to 2%/dry weight of yeast, among which sorbitan monostearate (MSS) is a routinely used standard additive.

The strains satisfy the test if the number of live yeasts after drying is at least equal to 80% of the number of live yeasts before drying.

According to another embodiment, the strain according to the invention has an application efficiency AE at least equal to 80%, preferably at least equal to 95% and even more preferably at least equal to 105% of the reference application efficiency. In the sense of the present invention, the term application efficiency of the strains refers to an efficiency of the yeasts obtained when cultured that is satisfactory in the final industrial use of said yeasts, i.e. an application efficiency AE at least equal to 90% of the application efficiency of a yeast obtained by culturing a reference strain for this use. A reference strain for a given use is a strain conventionally used for this use. Thus, the application efficiency for a strain cultured for the breadmaking industry will be the fermentative power, and the reference application efficiency will be that of the strain deposited on Feb. 12, 2003 at the Collection Nationale des Cultures de Microorganismes [National Collection of Cultures of Microorganisms] (CNCM, Pasteur Institute, 28 rue du Docteur Roux, 75724 Paris cedex 15) under No. I-2970, and it will be 120 mL of $CO_2$ released in 2 hours from 20 g of flour. The determination method is the so-called risograph method carried out by means of the Burrows and Harris fermentometer (Journal of Institute of Brewing, Vol. LXV, No. 1, Jan.-Feb. 25, 1959).

The biomass production is carried out using the so-called "aerobic Fed batch method" also referred to as "culturing in semi-continuous mode" or "semi-continuous culturing" or "semi-continuous mode," which here refers to culturing in a fermenter (or reactor) which is fed progressively with the culture medium, but from which no volume of medium is withdrawn. In such a method, the culture volume is variable (and generally increasing) in the fermenter, and the feed rate can be constant or variable.

The "Fed Batch" method is generally carried out under the conditions described in the reference book "Yeast Technology," Chapter 6, 2nd edition, 1991, G. Reed and T. W. Nagodawithana, published by Van Nostrand Reinhold, ISBN 0-442-31892-8.

For a strain cultured for biomass production, the application efficiency will be the production yield, and the reference application efficiency will be that of the strain deposited on Feb. 26, 1981 at the NCYC (National Collection of Yeast Cultures, Institute of Food Research, Norwich Research Park, Colney, Norwich, United Kingdom, NR4 7UA) under No. 995, and it will be 80% yield with respect to the C6 sugar used, or 80 g of yeast per g of poured molasses. The test will be carried by measuring the quantity of dry matter produced.

For a strain cultured for the production of alcohol, the application efficiency will be the ethanol production yield, and the reference application efficiency will be that of the strain deposited on Sep. 4, 2008 at the Collection Nationale des Cultures de Microorganismes (CNCM, Pasteur Institute, 28 rue du Docteur Roux, 75724 Paris cedex 15) under No. I-4071 and will be 0.40 g of ethanol produced per g of C6 sugar used. The quantities of ethanol and C6 sugar are measured by HPLC or enzymatic assays.

For a strain cultured for the production of yeast extract, the application efficiency will be the determination of the nitrogen content of the yeast extract obtained, and the reference application efficiency will be that of the yeast extract marketed by the company Bio Springer under the reference Springer 0203/0-MG-L and will be 10% nitrogen with respect to the dry matter. The nitrogen assay is done using the combustion method.

According to a particular embodiment, the strain has an application efficiency AE at least equal to 80%, preferably at least equal to 95% and even more preferably at least equal to 105% of the reference application efficiency, the application efficiency being selected from the group including the fermentative power, the yield of biomass, flavor, secondary metabolite, protein, ethanol production.

Advantageously, the strain according to the invention satisfies the drying test and has an application efficiency AE at least equal to 80% of the reference application efficiency.

The invention also relates to the following novel strains:
the yeast strain deposited on Aug. 23, 2012 at the Collection Nationale des Cultures de Microorganismes (CNCM, Pasteur Institute, 28 rue du Docteur Roux, 75724 Paris cedex 15) under No. I-4670
the yeast strain deposited on Aug. 23, 2012 at the Collection Nationale des Cultures de Microorganismes (CNCM, Pasteur Institute, 28 rue du Docteur Roux, 75724 Paris cedex 15) under No. I-4671.

These strains are breadmaking yeast strains each of which satisfies the growth test on xylose and the growth test on CP medium, and each of which has a fermentative power of at least 100 mL of $CO_2$ released in 2 hours from 20 g of flour, respectively. These strains also satisfy the drying test.

Another subject matter of the invention is a method for obtaining a yeast strain as defined above.

According to a first embodiment, the method comprises a step of genetic modification of a strain B having a reference application efficiency so as to make it capable of metabolizing a C5 sugar.

According to a second embodiment, the method comprises the crossing of a strain A capable of metabolizing a C5 sugar with a strain B having a reference application efficiency.

Regardless of the embodiment of the method according to the invention, said method can comprise at least one screening step making it possible to select a strain satisfying at least one of the tests selected from the growth test on xylose, the growth test on CP medium and the drying test, or having an application efficiency AE at least equal to 80%, preferably at least equal to 95% and even more preferably at least equal to 105% of the reference application efficiency of strain B.

The screening step can be carried out as the last step of the method of the invention.

According to the invention, the ability to metabolize a C5 sugar is reflected in the ability to produce ethanol from a medium comprising a C5 sugar under anaerobic conditions. The strains capable of metabolizing a C5 sugar are, in general, genetically modified strains in which each gene of the pentose pathway has been deregulated, the copies of the GRE3 gene coding for an aldose reductase are deleted, the native XKS1 gene coding for xylulokinase has been overexpressed, and which have undergone a directed evolution.

According to a form of the invention, a strain capable of metabolizing a C5 sugar is a strain comprising at least one copy of the *Pichia stipitis* XR gene coding for the enzyme xylose reductase, and at least one copy of the *Pichia stipitis* XDH gene coding for the enzyme xylose dehydrogenase.

According to another form of the invention, a yeast capable of metabolizing a C5 sugar is a yeast strain comprising at least one copy of an exogenous gene coding for a xylose isomerase and at least one copy of an exogenous gene coding for a xylitol dehydrogenase preferably originating from *Pichia stipitis*.

The xylose isomerase is a gene originating from *Clostridium, Piromyces, Bacteroides, Streptomyces, Haemophilus, Burkholderia, Enterococcus, Thermotoga, Fusobacterium, Geobacillus, Arthrobacter, Ciona, Physcomitrella, Cellvibrio, Chitinophaga, Saccharopolyspora* or *Salinibacter*, and it is preferably a gene originating from *Clostridium phytofermentans* or from *Piromyces* sp.

In addition, the strains capable of metabolizing a C5 sugar comprise the following modifications:

at least one copy, preferably at least two copies, of a gene coding for an aldose reductase, preferably the GRE3 gene, is deleted, and the endogenous gene coding for a xylulokinase, preferably the XKS1 gene, is placed under the control of a promoter of a gene not repressed by anaerobiosis or by the catabolic repression induced by any carbon source, and strongly expressed during the alcohol fermentation, at least one endogenous gene of the nonoxidative portion of the pentose phosphate pathway, preferably selected from the RPE1, RKI1, TKL1 and TAL1 genes, and particularly preferably all of these genes are placed under the control of a promoter of a gene not repressed by anaerobiosis or by the catabolic repression induced by any carbon source, and strongly expressed during the alcohol fermentation.

The methods for genetic modifications can be one of those described in WO 2011/128552 or in WO2012/72793.

According to the first embodiment, the method for genetic modification comprises introducing into the genome of the strain A at least one copy of a *Pichia stipitis* gene coding for a xylose reductase and at least one copy of a *Pichia stipitis* gene coding for a xylose dehydrogenase.

The method for genetic modification can, in addition, comprise introducing into the genome of the previously obtained strain at least one copy of an exogenous gene coding for a xylose isomerase, preferably originating from bacteria of the genus *Clostridium*, and preferably *Clostridium phytofermentans*, and at least one copy of a gene coding for a xylitol dehydrogenase originating from *Pichia stipitis*.

According to an embodiment of the hybridization method according to the invention, said method comprises the following steps:
selection of a strain (A) capable of metabolizing a C5 sugar;
selection of a strain (B) having performances compatible with an industrial application;
hybridization of the segregants of strain (A) with segregants of strain (B).

According to a variant, said hybridization method according to the invention comprises the following additional steps:
selection of a strain (A) capable of metabolizing a C5 sugar;
sporulation of said strain (A) in order to obtain a segregant X;
selection of a strain (B) having performances compatible with an industrial application;
sporulation of said strain (B) in order to obtain a segregant Y;
hybridization of X and Y.

Strain A is selected from genetically modified strains in which each gene of the pentose pathway has been deregulated, the copies of the gene coding for the aldose reductases are deleted, and which have undergone a directed evolution.

According to a form of the invention, a strain A capable of metabolizing a C5 sugar is a strain comprising at least one copy of the *Pichia stipitis* XR gene coding for the enzyme xylose reductase and at least one copy of the *Pichia stipitis* XDH gene coding for the enzyme xylitol dehydrogenase.

According to another form of the invention, a strain A capable of metabolizing a C5 sugar is a yeast strain comprising at least one copy of an exogenous gene coding for a xylose isomerase, and at least one copy of an exogenous gene coding for a xylitol dehydrogenase preferably originating from *Pichia stipitis*.

The xylose isomerase is a gene originating from *Clostridium, Piromyces, Bacteroides, Streptomyces, Haemophilus, Burkholderia, Enterococcus, Thermotoga, Fusobacterium, Geobacillus, Arthrobacter, Ciona, Physcomitrella, Cellvibrio, Chitinophaga, Saccharopolyspora* or *Salinibacter*, and preferably is a gene originating from *Clostridium phytofermentans* or from *Piromyces* sp.

In addition, the strains A capable of metabolizing a C5 sugar comprise the following modifications:
at least one copy, preferably at least two copies, of a gene coding for an aldose reductase, preferably the GRE3 gene, is deleted, and the endogenous gene coding for a xylulokinase, preferably the XKS1 gene, is placed under the control of a promoter of a gene not repressed by anaerobiosis or by the catabolic repression induced by any carbon source, and strongly expressed during the alcohol fermentation, at least one endogenous gene of the nonoxidative portion of the pentose phosphate pathway, selected preferably from the RPE1, RKI1, TKL1 and TAL1 genes, and particularly preferably all of these genes are placed under the control of a promoter of a gene not repressed by anaerobiosis or by the catabolic repression induced by any carbon source, and strongly expressed during the alcohol fermentation.

The methods for genetic modifications can be one of those described in WO 2011/128552 or in WO2012/72793.

Strain A can also be selected by a strain targeting method. Only the strains satisfying the growth test on xylose and/or the growth test on CP medium, as defined above, are selected.

Strain B can also be selected by a strain screening method. Only the strains having an application efficiency AE at least equal to 80%, preferably at least equal to 95% and even more preferably at least equal to 105% of the reference application efficiency will be selected.

When the strain is a breadmaking strain, strain (B) which will be selected will have a fermentative power greater than 5 mL·2 h$^{-1}$·g of flour$^{-1}$ preferably greater than 6 mL·2 h$^{-1}$·g of flour$^{-1}$ and even more preferably greater than 8 mL·2 h$^{-1}$·g of flour$^{-1}$.

The method using the steps for obtaining segregants can also comprise a step of screening segregant X and/or a step of screening of segregant Y. Only the segregants X that satisfy the growth test on xylose and/or the growth test on CP medium, as defined above, are selected. Only the segregants Y having an application efficiency AE at least equal to 80%, preferably at least equal to 95% and even more preferably at least equal to 105% of the reference application efficiency will be selected.

Preferably, segregant X is selected from the strains deposited in the Collection Nationale des Cultures de Microorganismes (CNCM, Institut Pasteur, 28 rue du Docteur Roux, 75724 Paris cedex 15) on Aug. 23, 2012 under No. I-4672 and I-4673, and segregant Y is the strain deposited at the Collection Nationale des Cultures de Microorganismes (CNCM, Institut Pasteur, 28 rue du Docteur Roux, 75724 Paris cedex 15) on Aug. 23, 2012 under No. I-4669.

Another subject matter of the invention is an aerobic "Fed batch" method for producing yeasts on a substrate comprising at least one C5 sugar from a strain as described above. By aerobic "Fed Batch" method it is referred to a "culturing in semi-continuous mode" or "semi-continuous culturing" or "semi-continuous mode," which here refers to culturing in a fermenter (or reactor) which is progressively fed with the culture medium, but from which no volume of medium is withdrawn. In such a method, the culture volume is variable (and generally increasing) in the fermenter, and the feed rate can be constant or variable.

The "Fed Batch" method is generally carried out under the conditions described in the reference book "Yeast Technology," Chapter 6, 2nd edition, 1991, G. Reed and T. W. Nagodawithana, published by Van Nostrand Reinhold, ISBN 0-442-31892-8.

According to the invention, the rate of multiplication is generally 1.16. In general, the rate of use of C5 sugars by the strains of the invention depends on the nature of these strains and can reach up to 100% under certain conditions. Thus, a strain intended for a final application in breadmaking can, in its multiplication, use up to 50% of the C5 sugars included in the fermentation substrate, whereas a strain intended for an application of ethanol production can use up to 100% of the C5 sugars.

Another subject matter of the invention is the use of the yeasts obtained in at least one industrial application selected from breadmaking, biomass production, flavor production, the production of secondary metabolites, protein production, RNA production, ethanol production, brewing or the production of yeast extract.

The following examples illustrate the invention without limiting its scope.

EXAMPLES

Example 1

Preparation of Segregants X

In order to obtain segregants of the strain CNCM I-4538, the latter was cultured for 24 hours in YPG medium containing 10 g/kg of Yeast Extract (EXL) type J100, 10 g/kg of peptone and 20 g/kg of glucose. The suspension of cells that was obtained was then transferred to a Petri dish containing SAA medium consisting of 20 g/kg of agarose and of 7.5 g/kg of sodium acetate. After 5 days of incubation at 30° C., the tetrads are dissected using a micromanipulator. The dishes thus prepared are incubated for 48 hours at 30° C.

One of the limits to the use of the segregants obtained relates to their sexual signal. Indeed, at the time of the construction by molecular biology of the strains capable of fermenting xylose, some genes essential for this pathway were introduced in a locus that is genetically linked to Mat alpha. This point therefore implies that all the segregants originating from the strain deposited at the Collection Nationale des Cultures de Microorganismes (CNCM, Institut Pasteur, 28 rue du Docteur Roux, 75724 Paris cedex 15) on Oct. 5, 2011 under reference CNCM I-4538, and which are capable of metabolizing xylose, have the Mat alpha signal. In order to eliminate this limitation, the sexual signal of these segregants was changed. For this purpose, we used a process that exists in nature. Indeed, some wild yeasts, when they are in the haploid state, are capable of changing sexual signal. This process occurs under the action of the HO recombinase. The latter is not functional in the strain deposited at the CNCM under reference CNCM I-4538, and consequently it also does not function in this strain. We introduced a replicative plasmid containing a gene coding for a functional HO recombinase into the segregants of interest. This method is based on the studies of Herskowitz and Jensen published in 1991. The HO gene carried by the plasmid in question was placed under the dependency of a promoter induced by galactose. The segregants thus transformed were incubated for 16 hours in a medium containing 10 g/kg of EXL type J100, 10 g/kg of Peptone and 20 g/kg of galactose. The cells were then spread on a solid medium containing 10 g/kg of EXL type J100, 20 g/kg of agarose and 20 g/kg of glucose. After having obtained clones, the change in sexual signal was verified by carrying out a PCR on the locus of expression of the sexual signal. This reaction is carried out using as matrix the genomic DNA of each potential segregant. The oligonucleotides are, on the one hand, a primer specific to the MAT locus expressed on chromosome III of the yeast (primer Mat1: AGTCACAT-CAAGATCGTTTATGG) (SEQ ID NO: 1) and two other primers, one specific to Mat alpha (primer Mat2: GCACG-GAATATGGGACTACTTCG) (SEQ ID NO: 2) and the other specific to Mat a (primer Mat3: ACTCCACTTCAAG-TAAGAGTTTG) (SEQ ID NO: 3).

The Mat a genotype of the yeasts is characterized by the presence of an amplicon of 544 base pairs which is detectable on agarose gel at 0.8%.

The results obtained are presented in FIG. 1.

Example 2

Preparation of Segregants Y and Verification of the Capacity of the Segregants to Transmit a High Fermentative Power after Hybridization Preparation of the segregant: the segregant deposited at the CNCM under No. I-4669 was prepared from the breadmaking strain deposited at the CNCM under No. I-2970. The preparation method used is identical to the one described in Example 1.

Verification of the transmission: hybrids 4539 and 4550 were prepared by hybridization of the segregants originating from the breadmaking strains deposited at the NCYC under No. 955 and at the CNCM under No. I-2970.

The fermentative powers on Normal Dough (ND) and Sweetened Dough at 2 g (SD 2 g) indicated in the following table show that the segregant I-4669 can transmit a high fermentative power after hybridization.

TABLE 1

| Strains | I-2970 | NCYC-995 | 4539 | 4550 |
| --- | --- | --- | --- | --- |
| Power on ND | 161 | 146 | 187 | 167 |
| Power on SD 2 g | 139 | 117 | 155 | 148 |

Example 3

Hybridization

The different segregants prepared were crossed as indicated in the following table:

TABLE 2

| | Crosses performed | | | | |
| --- | --- | --- | --- | --- | --- |
| | | Mat alpha | | | |
| | X10S3 | X10S2 CNCM No. I-4673 | X10S1 CNCM No. I-4672 | PS27 | Ps28 |
| Mat a  X10S4 | | | | HC5-G | HC5-H |
| X10S5 | | | | HC5-I | HC5-J |
| X10S6 | | | | HC5-K | HC5-L |

TABLE 2-continued

Crosses performed

| | | Mat alpha | | | |
|---|---|---|---|---|---|
| | X10S3 | X10S2 CNCM No. I-4673 | X10S1 CNCM No. I-4672 | PS27 | Ps28 |
| PS316 I-4669 | HC5-A | HC5-C I-4671 | HC5-B I-4670 | | |
| P3S8 | HC5-D | HC5-F | HC5-E | | |

Example 4

Screening

The hybrid stains obtained in Example 3 above were subjected to the following different screenings:

1/ Growth Test on Xylose

This first test concerns the capacity to multiply using xylose as carbon source.

In order to determine the capacity of the strains to multiply using xylose as carbon source, we inoculated them at $2\times10^6$ cells/mL in 50 mL of YFX medium which composition is given below, and maintained them at 30° C. under stirring at 150 rpm.

Figure 2:
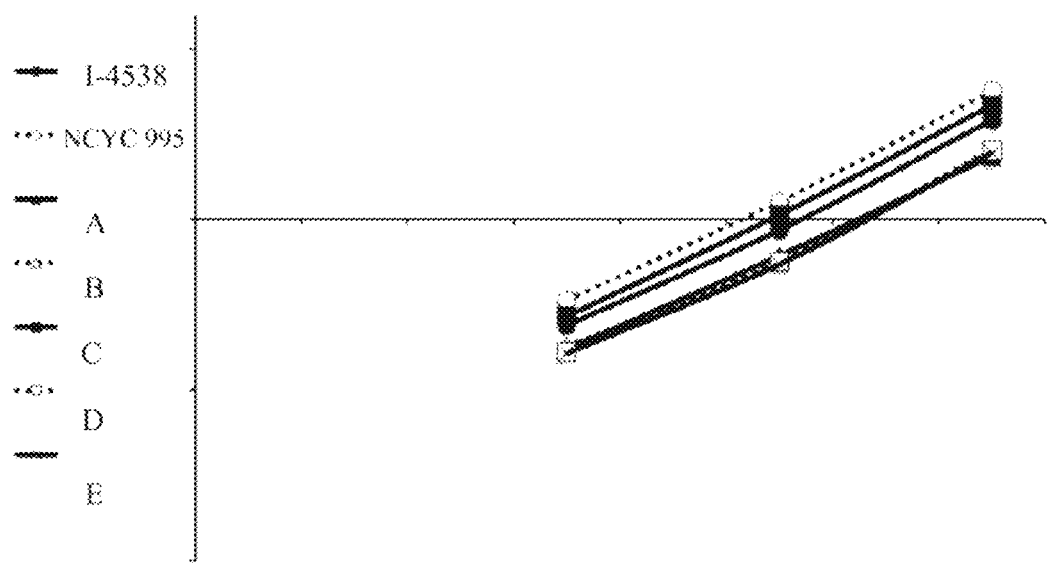
FIG. 2 is a graph representing the variation in the turbidity of the medium expressed in Log 10($OD_{lambda-600\ nm}$) as a function of culture time (expressed in hours) at 30° C. and 150 rpm in CP medium.

The variation in biomass is determined by monitoring the turbidity measured with a spectrophotometer at a wavelength of 600 nm. The result of this monitoring is represented in FIG. 2.

The variation in biomass on the YFX medium allowed us to select 4 strains. They are the strains HC5-A, HC5-B, HC5-C and HC5-D which have a good ability to use xylose as carbon source. In addition, these strains are capable of processing xylose rapidly, while hybrids HC5-K and HC5-L were not kept because of their delay in initiating their growth on xylose.

2/ Growth Test on CP Medium

Figure 3:
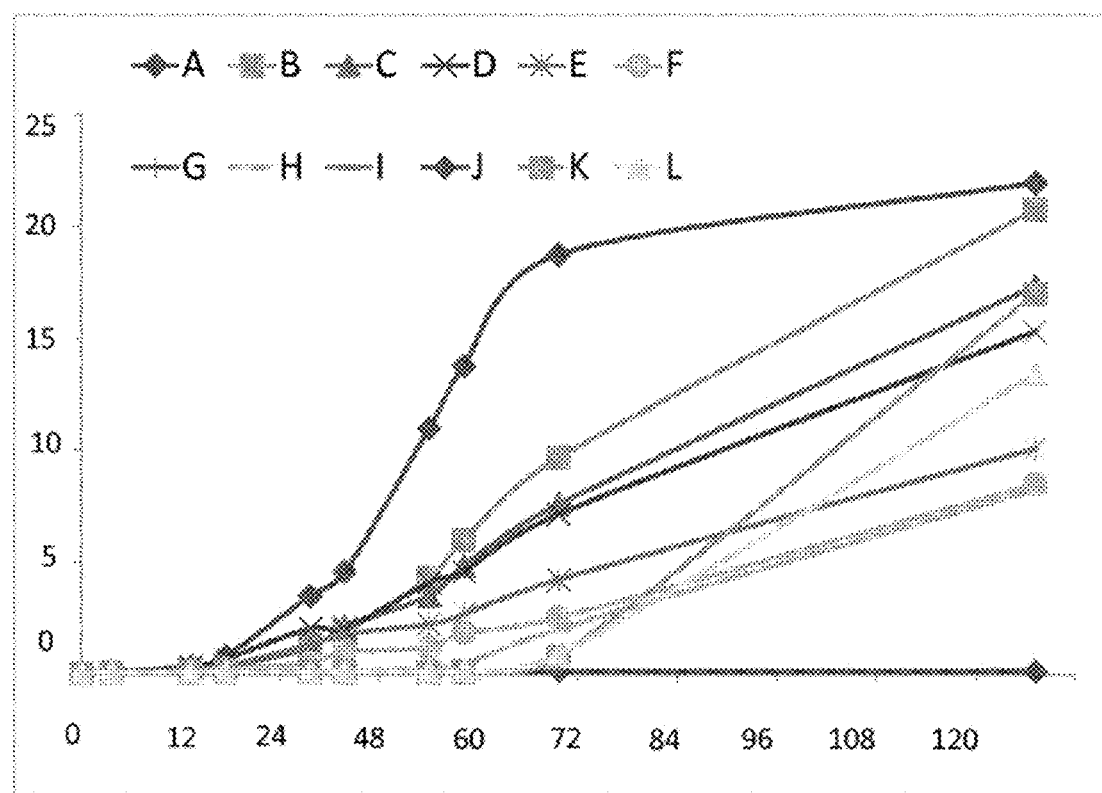
FIG. 3 is a graph representing the turbidity of the medium expressed in OD at a wavelength of 600 nm, as a function of culture time, expressed in hours, at 30° C. and at 150 rpm in YFX medium.

Another important criterion is the maximum speed of multiplication of the cells. In order to determine it, the yeasts were inoculated in 50 mL of CP medium with $2\times10^6$ cells per mL. This medium is very rich, since it contains 10 g/kg of EXL and 10 g/kg of bactopeptone as well as 100 g/kg of sucrose. The variation in turbidity is measured by spectrophotometry at 600 nm. Next, the maximum speed of multiplication is analyzed by identifying the period during which the biomass grows exponentially. FIG. 3 represents the variation in turbidity on a logarithmic scale and as a function of the culturing time.

In the interval between 3.5 and 7.5 hours, the variation in turbidity is exponential, which is confirmed by the linear appearance on our graph which uses a logarithmic scale. The speed of multiplication is defined as the derivative of the variation in turbidity at 600 nm as a function of time. Now, as the various lines appear to be parallel, this suggests that the speeds of multiplication appear to be comparable to those of the strain deposited at NCYC under reference NCYC 995 and of the strain deposited at the CNCM under reference CNCM I-4538 on this medium.

3/ Test of the Fermentative Power after a Pseudo Fedbatch

Figure 4:
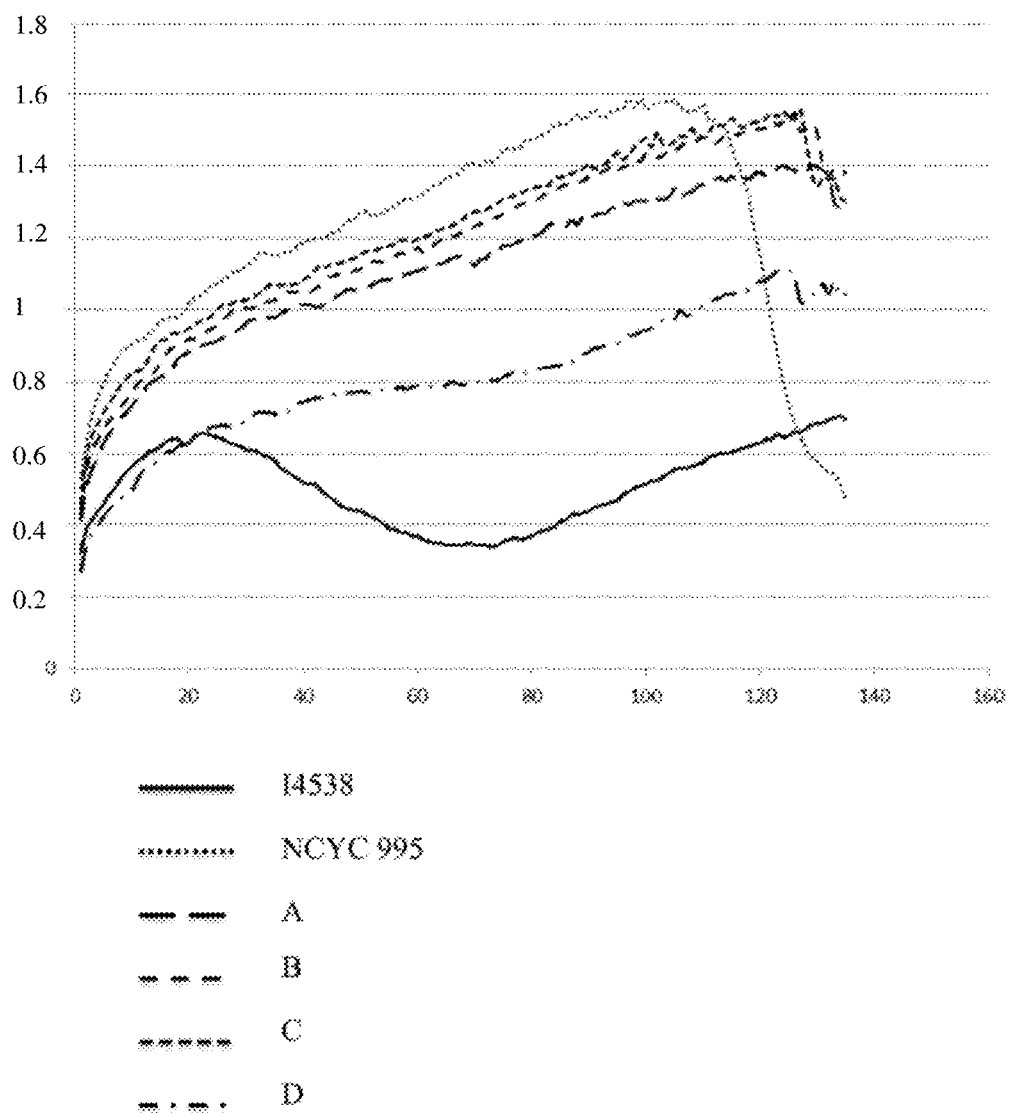
FIG. 4 is a graph representing the gaseous release expressed in mL per minute on normal dough versus time expressed in minutes.

Hybrides HC5-B and HC5-C (strains I-4670 and I-4671) were propagated using raffinose as carbon source. The use of this trisaccharide makes it possible to deliver the sugar progressively to the yeast. Indeed, raffinose is hydrolyzed slowly by the invertase of the yeasts. After having standardized the quantities of biomass of the different productions by measuring the quantity of dry yeast material per unit of volume using a SMART System5™ apparatus (CEM corporation, USA), we analyzed the gaseous release using a risograph fermentometer. The variation in gaseous releases for a test on normal dough, represented in FIG. 4, is carried out as follows:

A suspension of yeast is prepared as follows: the quantity equivalent to 1 g of dry matter of the yeast to be tested is suspended and brought up to 100 mL with a solution containing 27 g/L of NaCl and 4 g/L of $(NH_4)_2SO_4$.

15 mL of the above suspension (that is 150 mg of dry yeast matter) are equilibrated at a temperature of 30° C. for 15 minutes.

To this suspension, 20 g of flour, equilibrated beforehand overnight at 30° C., are added. The whole is homogenized for a duration of 35 seconds.

The dough formed is incubated in a hermetically closed container placed at 30° C. The gaseous release (expressed in mL under 760 mm Hg) is recorded for a total duration of 120 minutes.

The protocol of the measurement of the gaseous release for a test in Sweetened Dough (SD) is identical to that followed for ND except that sugar (here 2 g) is added with the other dry ingredients.

The profiles obtained show that the catabolic repression is high in the strain deposited at the CNCM under reference CNCM I-4538, which induces an important diauxie phenomenon referred to as "maltose lag" which disqualifies it for the breadmaking applications. On the other hand, it should be noted that hybrids HC5-A, B, C and D, although slower than the strain deposited at the NCYC under No. NCYC 995, seem to have profiles of interest. Hybrides HC5-B and HC5-C (strains I-4670 and 4671) yield the best results.

Example 5

Each of the strains deposited under No. I-4670 and No. I-4671 was subjected to a growth test on xylose, to a growth test on CP medium, and their fermentative power was measured.

The results obtained are presented in the table below:

| Strain | CNCM No. I-4670 | CNCM No. I-4671 |
|---|---|---|
| Growth on xylose (speed of multiplication) | 3.5 hours/generation | 6 hours/generation |
| Growth of the CP medium (speed of multiplication) | 0.71 | 0.66 |
| Fermentative power | 139 | 143 |

Example 6

Each of the strains deposited under No. I-4670 and No. I-4671 was multiplied according to an aerobic Fed batch method for 18 hours. The fermentative powers of the yeasts obtained after drying were measured according to a Normal Dough (ND) test and according to a Sweetened Dough 2 grams test (SD 2 g). The results obtained are reproduced below:

|  | AE of the strain referenced | | |
|---|---|---|---|
|  | NCYC 995 | I-4670 | I-4671 |
| culture medium | 100% C6 | C5/C6 of 0.42 | C5/C6 of 0.42 |
| Production yield | 79.2% | 65.7% | 66.0% |
| Fermentative power ND | 118 | 119 | 120 |
| Fermentative power SD 2 g | 114 | 116 | 107 |

The invention claimed is:

1. A yeast strain of the *saccharomyces* genus, capable of multiplying under aerobic conditions on a substrate comprising at least one C5 sugar, wherein said strain satisfies a growth test on xylose or has a maximum speed of multiplication such that it satisfies a growth test on CP medium, and wherein, in its genome
   the expression of genes RPE1, RKI1, TKL1 and TAL1 of the pentose pathway has been placed under the control of a promoter of a gene not repressed by anaerobiosis or by the catabolic repression induced by any carbon source, and expressed during alcohol fermentation;
   at least one copy of the GRE 3 gene coding for an aldose reductase is deleted;
   the native XKS1 gene has been overexpressed;
   at least one copy of a *Pichia Stipitis* gene coding for a xylitol dehydrogenase has been introduced;
   and at least one copy of a gene coding for a xylose isomerase has been introduced.

2. The strain according to claim 1, wherein the gene coding for the xylose isomerase originates from bacteria of the genus *Clostridium*.

3. The strain according to claim 1, wherein said strain satisfies a growth test on xylose and has a maximum speed of multiplication such that it satisfies a growth test on CP medium.

4. The strain according to claim 1, selected from the genus *Saccharomyces*.

5. The strain according to claim 1, wherein said strain satisfies a drying test.

6. The strain according to claim 1, wherein said strain has an application efficiency AE at least equal to 80% of the reference application efficiency.

7. The strain according to claim 6, wherein said application efficiency is selected from the group comprising the fermentative power, the viability, the yield of biomass, flavor, secondary metabolite, protein, RNA or ethanol production.

8. The yeast strain according to claim 1, which is a breadmaking yeast strain.

9. The strain according to claim 1, wherein said strain is a breadmaking yeast which application efficiency is the fermentative power and is at least equal to 95% of the reference fermentative power which is 100 mL of $CO_2$ in 2 hours from 20 g of flour.

10. The yeast strain according to claim 9, deposited under the Budapest Treaty at the CNCM on Aug. 23, 2012 under No. I-4670.

11. The yeast strain according to claim 9, deposited under the Budapest Treaty at the CNCM on Aug. 23, 2012 under No. I-4671.

* * * * *